US011218792B2

(12) United States Patent
Monahan et al.

(10) Patent No.: US 11,218,792 B2
(45) Date of Patent: *Jan. 4, 2022

(54) EARPIECE PASSIVE NOISE ATTENUATING

(71) Applicant: Bose Corporation, Framingham, MA (US)

(72) Inventors: Michael Monahan, Southborough, MA (US); Ryan C. Silvestri, Franklin, MA (US); Eric M. Wallace, Andover, MA (US); Kevin P. Annunziato, Medway, MA (US)

(73) Assignee: Bose Corporation, Framingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/265,685

(22) Filed: Feb. 1, 2019

(65) Prior Publication Data
US 2019/0253782 A1 Aug. 15, 2019

Related U.S. Application Data

(63) Continuation of application No. 15/137,632, filed on Apr. 25, 2016, now Pat. No. 10,334,344, which is a (Continued)

(51) Int. Cl.
H04R 1/10 (2006.01)
A61F 11/08 (2006.01)
(Continued)

(52) U.S. Cl.
CPC ............ H04R 1/1016 (2013.01); A61F 11/08 (2013.01); H04R 1/1058 (2013.01); H04R 1/105 (2013.01);
(Continued)

(58) Field of Classification Search
CPC ........ H04R 1/10; H04R 1/1016; H04R 1/105; H04R 1/1058; H04R 1/1066; H04R 25/02;
(Continued)

(56) References Cited

U.S. PATENT DOCUMENTS 1,668,890 A    5/1928  Curran et al.
2,492,183 A *  12/1949 Rosenblatt .............. A61F 11/08
                                              128/864
(Continued)

FOREIGN PATENT DOCUMENTS

CN    1173810    2/1998
CN    2459840    11/2001
(Continued)

OTHER PUBLICATIONS

European Search Report; EP 17 16 8500; dated Aug. 14, 2017; 8 pages.
(Continued)

Primary Examiner — Alexander Krzystan
(74) Attorney, Agent, or Firm — Fish & Richardson P.C.

(57) ABSTRACT

An earpiece with structure for positioning and retaining the earpiece and with structure for sealing against the entrance to the ear canal to provide passive noise attenuation. The positioning and retaining structure engages features of the lateral surface of the ear. The structure for sealing against the entrance to the ear canal includes a conical structure.

21 Claims, 7 Drawing Sheets

Related U.S. Application Data continuation of application No. 14/272,845, filed on May 8, 2014, now Pat. No. 9,398,364, which is a continuation of application No. 13/193,288, filed on Jul. 28, 2011, now Pat. No. 8,737,669.

(51) Int. Cl.
  *H04R 25/00* (2006.01)
  *H04R 25/02* (2006.01)

(52) U.S. Cl.
  CPC ............ *H04R 1/1083* (2013.01); *H04R 25/02* (2013.01); *H04R 25/652* (2013.01); *H04R 25/654* (2013.01); *H04R 25/656* (2013.01)

(58) Field of Classification Search
  CPC .... H04R 25/60; H04R 25/604; H04R 25/608; H04R 25/65; H04R 25/652; H04R 25/656
  USPC .................................................. 381/385, 182
  See application file for complete search history.

(56) References Cited

U.S. PATENT DOCUMENTS

| | | | |
|---|---|---|---|
| 2,908,343 A | 10/1959 | Hummert | |
| 4,055,233 A | 11/1977 | Huntress | |
| 4,091,067 A | 5/1978 | Kramer | |
| 4,878,560 A * | 11/1989 | Scott | H04R 1/1016 181/130 |
| 6,914,997 B2 | 7/2005 | Macdonald et al. | |
| 7,856,111 B2 | 12/2010 | Balke et al. | |
| 7,986,803 B1 | 7/2011 | DeKalb | |
| 8,331,593 B2 | 12/2012 | Stemming et al. | |
| 9,398,364 B2 | 7/2016 | Monahan et al. | |
| 10,334,344 B2 * | 6/2019 | Monahan | H04R 1/1016 |
| 2007/0116309 A1 | 5/2007 | Smith | |
| 2008/0002835 A1 | 1/2008 | Sapiejewski et al. | |
| 2008/0144877 A1* | 6/2008 | Ham | H04R 1/105 381/379 |
| 2009/0041284 A1* | 2/2009 | Tanaka | H04R 1/1016 381/370 |
| 2009/0123010 A1* | 5/2009 | Cano | H04R 1/1016 381/318 |
| 2010/0027824 A1* | 2/2010 | Atamaniuk | H04R 1/105 381/322 |
| 2011/0176700 A1 | 7/2011 | Hashimoto | |
| 2011/0261988 A1* | 10/2011 | Kromann | H04R 1/1016 381/380 |
| 2012/0217087 A1* | 8/2012 | Ambrose | H04R 1/1016 181/130 |
| 2015/0215693 A1* | 7/2015 | Sandanger | H04R 1/1016 381/380 |
| 2019/0223747 A1* | 7/2019 | Chou | A61B 5/681 |

FOREIGN PATENT DOCUMENTS

| | | |
|---|---|---|
| CN | 101094760 | 12/2007 |
| CN | 101297593 | 10/2008 |
| CN | 102132587 | 7/2011 |
| DE | 202011002165 | 5/2011 |
| EP | 1 874 080 | 1/2008 |
| EP | 2071867 | 11/2017 |
| JP | 074473 | 8/1927 |
| JP | A 63-079500 | 4/1988 |
| JP | A 2008-17473 | 1/2008 |
| JP | A 2008-92356 | 4/2008 |
| WO | WO 2007/014950 | 2/2007 |
| WO | WO 2009/086555 | 7/2009 |
| WO | WO 2009/153221 | 12/2009 |
| WO | WO 2010/031775 | 3/2010 |
| WO | WO 2010/040350 | 4/2010 |
| WO | WO 2010/040351 | 4/2010 |
| WO | WO 2010/131426 | 11/2010 |

OTHER PUBLICATIONS

Japanese Office Action dated Jul. 4, 2016 for Japanese Patent Application No. 2015-154126.
Notification of Second Office Action w/ English Translation; CN Appln. No. 2014104239492; dated Aug. 29, 2017; 18 pages.
Notification of Third Office Action w/English Translation; CN Appln. No. 2014104239492; dated Jan. 24, 2018; 13 pages.
Office Action in corresponding EP Application No. 17 168 500.1 dated Jun. 8, 2018, pp. 1-6.
Office Action in corresponding EP Application No. 17 168 520.9 dated Jun. 7, 2018, pp. 1-6.
Petition for Inter Partes Review, *Freebit AS*, Petitioner, v. *Bose Corporation*, Patent Owner, U.S. Pat. No. 8,311,253.
Petition for Inter Partes Review, *Freebit AS*, Petitioner, v. *Bose Corporation*, Patent Owner; U.S. Pat. No. 9,036,853.
Petition for Inter Partes Review, *Freebit AS*, Petitioner, v. *Bose Corporation*, Patent Owner; U.S. Pat. No. 8,254,621.
Chinese Office Action in Chinese Appln. No. 2016105673488, dated Aug. 30, 2019, 2 pages (English translation only).
EPO Communication in EP Application No. 12741458.9, dated Jun. 24, 2019, 6 pages.
First Chinese Office Action dated Mar. 2, 2017 for Chinese Patent application No. 201410423949.2, 7 pages.
First Office Action; CN Appln. No. 201710358826.9; dated Oct. 24, 2018; with English Translation; 10 pages.
Notice of Reasons for Rejection with English Translation; JP Appln. No. 2017-074265; dated Apr. 16, 2018; 11 pages.
Extended European Search Report in EP Application No. 18212433. 9-1210, dated Mar. 22, 2019, 7 pages.
Extended European Search Report in EP Application No. 18212436. 2-1210, dated Mar. 20, 2019, 7 pages.
Extended European Search Report in EP Application No. 18212439. 6, dated Mar. 20, 2019, 7 pages.
EP Extended European Search Report in European Appln. No. 21154253.5, dated Jun. 17, 2021, 9 pages.

* cited by examiner

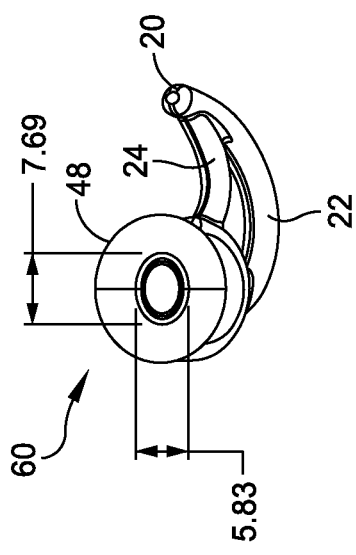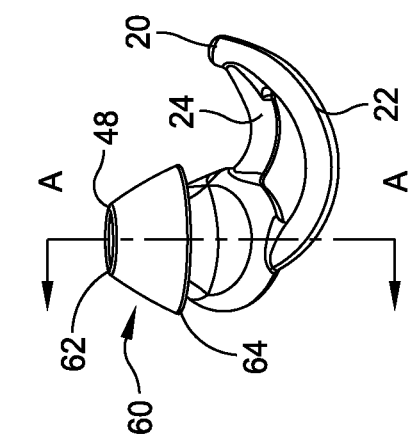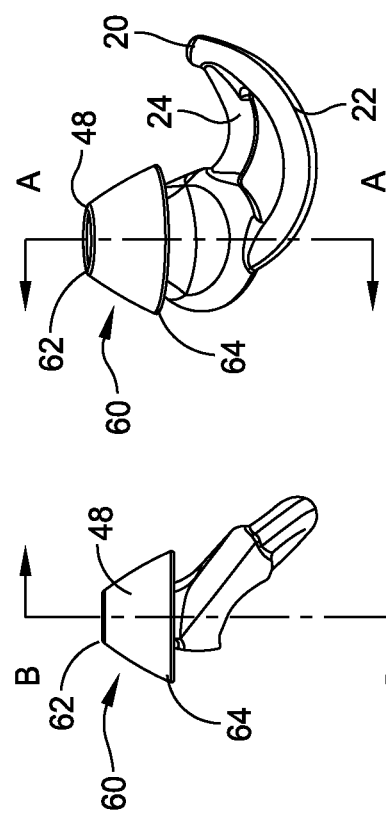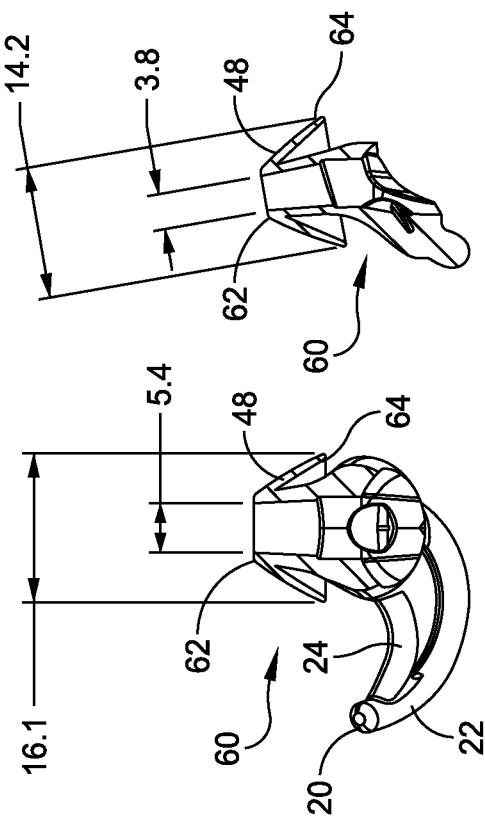

EARPIECE PASSIVE NOISE ATTENUATING

CROSS-REFERENCE TO RELATED APPLICATIONS

This application is a continuation of and claims priority to U.S. patent application Ser. No. 15/137,632 filed Apr. 25, 2016, which is a continuation of and claims priority to U.S. patent application Ser. No. 14/272,845, filed May 8, 2014 (now U.S. Pat. No. 9,398,364), which is a continuation of and claims priority to U.S. patent application Ser. No. 13/193,288 (now U.S. Pat. No. 8,737,669), filed Jul. 28, 2011, the entire contents of which are incorporated herein by reference.

BACKGROUND

This specification describes a structure for providing passive noise attenuation by an in-ear earpiece and for positioning and retaining the earpiece in the ear.

SUMMARY

In one aspect, an in-ear earpiece includes an acoustic driver; an acoustic passage to conduct sound waves radiated by the acoustic driver to an ear canal of a user; a positioning and retaining structure to engage features of the lateral surface of an ear of the user to position the earpiece and to hold the earpiece in place without any structure external to the earpiece; and a substantially conical structure configured so that the smaller end of the conical structure is smaller than the entrance to an ear canal of a user and so that the larger end of the conical structure is larger than the entrance to the ear canal of the user, formed of material that conforms to the entrance to the ear canal to seal the ear canal. The material may have a hardness of 30 Shore A or less. The material may have a modulus of 2 gf/mm or less. The material may be silicone rubber. The material may be a thermoplastic elastomer. The material may be a thermoplastic polyurethane. The positioning and retaining structure may include a first leg and a second leg attached to each other at an attachment end to form a tip and attached to a body of the earpiece at the other end. The positioning and retaining structure may provide at least three modes for preventing clockwise rotation of the earpiece past a rotational position. The modes may include an extremity of the tip contacting the base of the helix; the extremity of the tip becoming wedged under the anti-helix in the cymba concha region; and the inner leg contacting the base of the helix. The positioning and retaining structure may include an inner leg and an outer leg. The inner leg and the outer leg may be attached at an attachment end to the body and attached at a joined end to each other. With the earpiece in its intended position, the outer leg may be urged against the anti-helix at the rear of the concha, the body engages the ear canal; and at least one of the tip is under the anti-helix; or a portion of at least one of the body and the outer leg are under the anti-tragus. The positioning and retaining structure may include an inner leg and an outer leg attached at attachment end to each other and at a second end to an earpiece body. The inner leg and outer leg may be arranged to provide at least three modes for preventing clockwise rotation of the earpieces. The modes may include the tip contacts the base of the helix; the tip becomes wedged under the anti-helix; and the inner leg contacts the base of the helix. The inner leg and the outer leg may be further arranged so that with the earpiece in its intended position, the outer leg is urged against the anti-helix at the rear of the concha, the body engages the ear canal; and at least one of the tip is under the anti-helix; or a portion of at least one of the body and the outer leg are under the anti-tragus. The substantially conical structure may include an opening therethrough to conduct sound waves from the acoustic driver to the ear canal. The opening may be substantially elliptical in cross-section. The substantially conical structure may taper substantially linearly from the large end to the small end. The substantially conical structure may have a substantially uniform thickness. The material of the positioning and retaining structure of the user may have a different hardness than the substantially conical structure. The material of the structure to conduct sound waves radiated by the acoustic driver to an ear canal of a user may have a different hardness than the material of the positioning and retaining structure of the user and than the material of the substantially conical structure.

In another aspect, an eartip for an in-ear earpiece includes positioning and retaining structure to engage features of the lateral surface of an ear to position the earpiece and to hold the earpiece in place without any structure external to the earpiece and a substantially conical structure configured so that the smaller end of the conical structure is smaller than the entrance to an ear canal of a user and so that the larger end of the conical structure is larger than the entrance to the ear canal of the user, formed of material that conforms to the entrance to the ear canal to seal the ear canal. The positioning and retaining structure and the substantially conical structure may include the same material. The positioning and retaining structure and the substantially conical structure may be a unitary structure.

Other features, objects, and advantages will become apparent from the following detailed description, when read in connection with the following drawing, in which:

BRIEF DESCRIPTION OF THE SEVERAL VIEWS OF THE DRAWING

FIGS. 7A-7C are views of a portion of the earpiece of FIGS. 2 and 5A-5D; and

FIGS. 8A and 8B are cross-sections of the earpiece portions of FIGS. 7A-7C.

DETAILED DESCRIPTION

This specification describes an in-ear earpiece that is designed to fit in the right ear. An earpiece that is designed to fit in the left ear is a mirror image of the earpiece described below, and operates according to the same principles, and is not described herein.

Figure 1A:
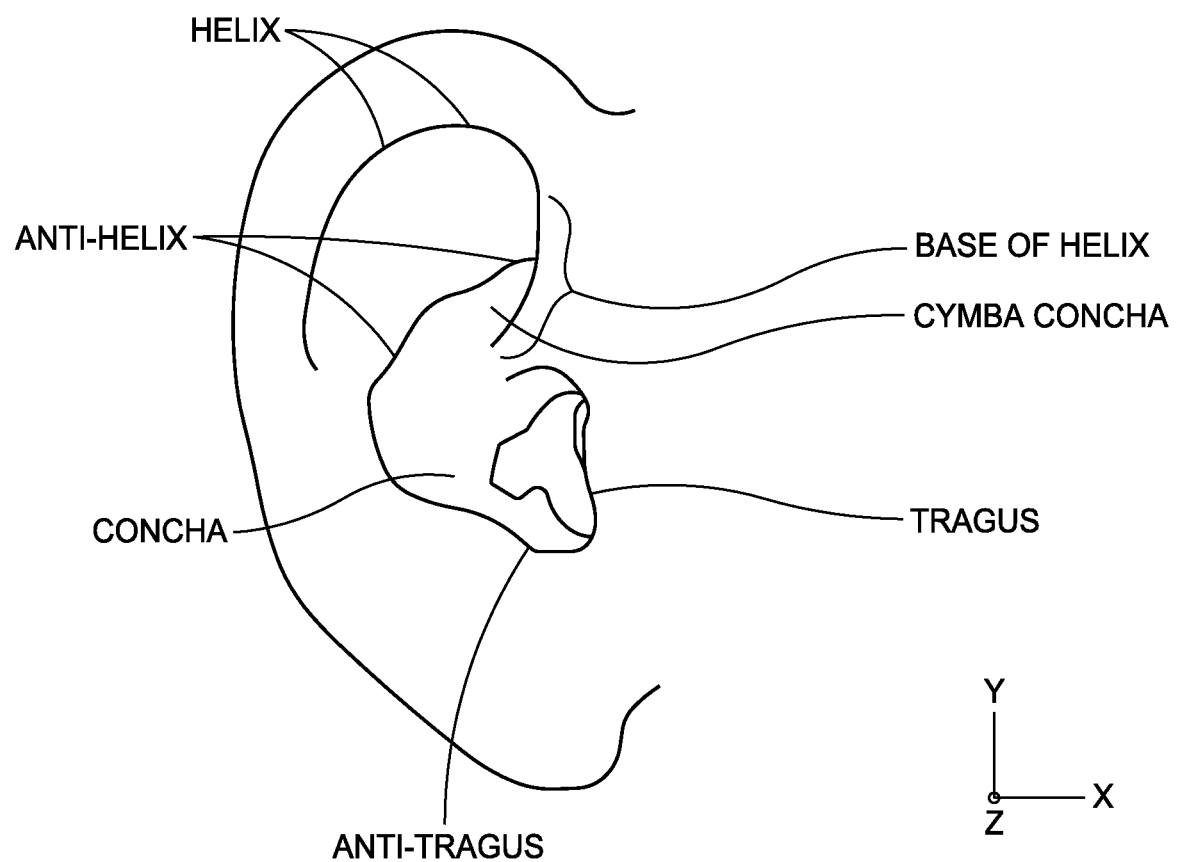
FIG. 1A is a view of the lateral surface of the human ear.
Figure 1B:
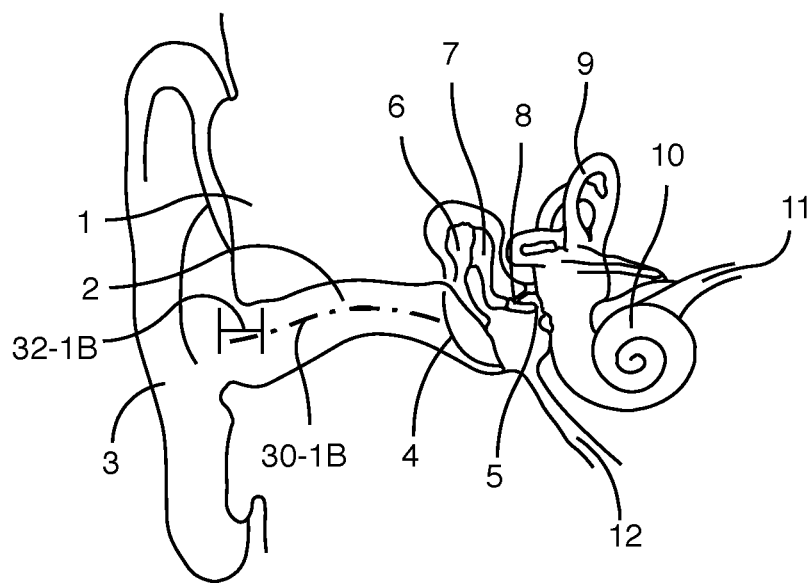
FIGS. 1B and 1C are exemplary cross-sections of the human ear.
Figure 1C:
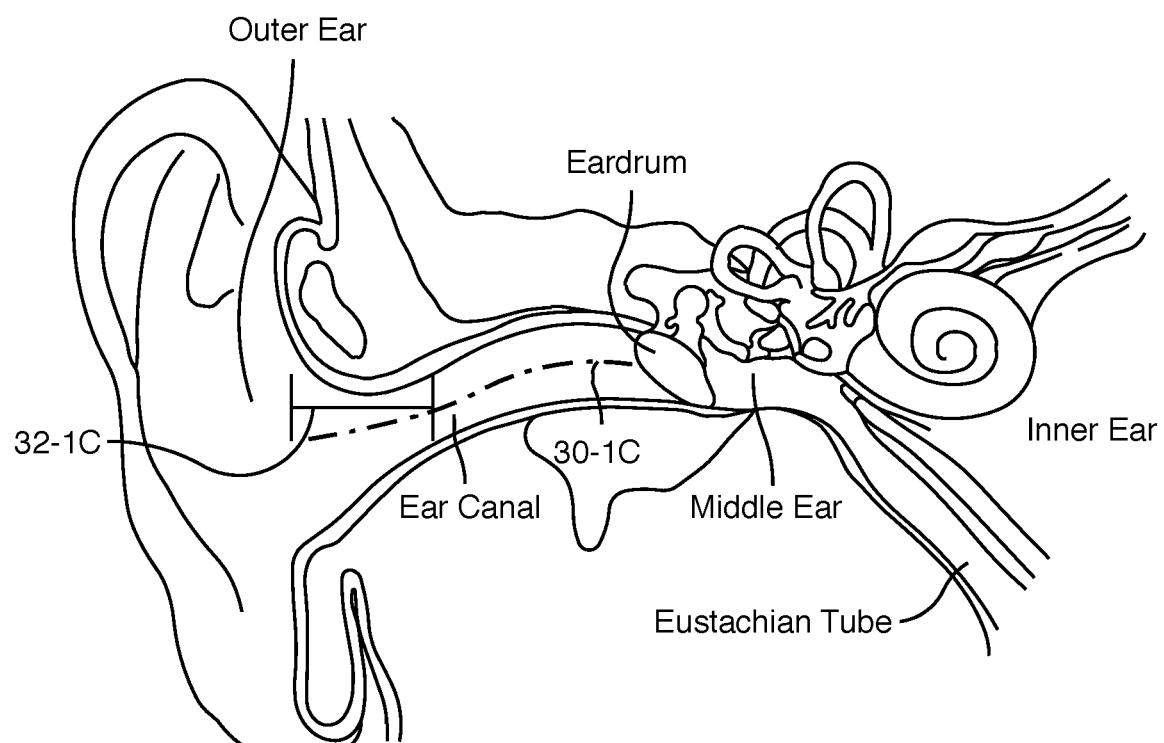

FIG. 1A shows the lateral surface of a human right ear, with some features identified. There are many different ear sizes and geometries. Some ears have additional features that are not shown in FIG. 1A. Some ears lack some of the features that are shown in FIG. 1A. Some features may be more or less prominent than are shown in FIG. 1A. FIGS. 1B and 1C show two exemplary cross-sections of the human ear, with some features identified. The ear canal is an irregularly shaped cylinder with a variable cross sectional area and a centerline that is not straight. Among the features identified is the entrance to the ear canal and the main portion of the ear canal. In this specification the entrance to the ear canal refers to the portion of the ear canal near the concha where the walls of the ear canal are substantially non parallel to the centerline of the ear canal. The precise structure of the human ear varies widely from individual to individual. For example, in the cross section of FIG. 1B, there is a relatively sharp transition from ear canal walls that are non-parallel to a centerline 30-1B of the ear canal to walls that are substantially parallel to a centerline of the ear canal, so the entrance 32-1B to the ear canal in relatively short. In the cross-second of FIG. 1C, there is a more gradual transition from walls that are non-parallel to a centerline of the ear canal to walls that are substantially parallel to a centerline 30-1C of the ear canal, so the entrance 32-1C to the ear canal is relatively long.

Figure 2:
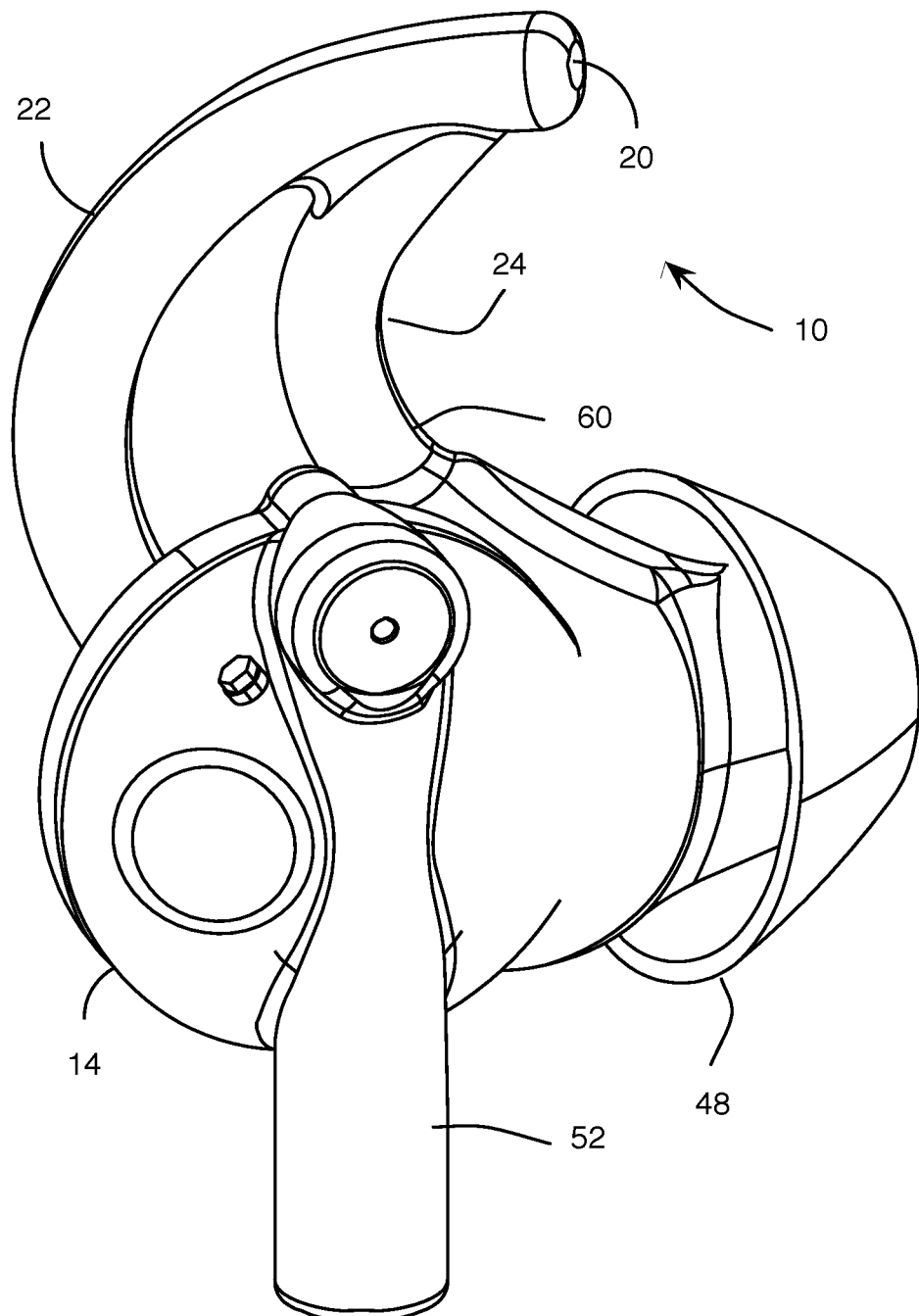
FIG. 2 is an isometric view of an earpiece.

FIG. 2 shows an earpiece 10. The earpiece 10 may include a stem 52 for positioning cabling and the like, an acoustic driver module 14, and a tip 60 (more clearly identified in FIGS. 5A-5D). Some earpieces may lack the stem 52 but may include electronics modules (not shown) for wireless communicating with external devices. Other earpieces may lack the stem and the acoustic driver module and may function as passive earplugs. The tip 60 includes a positioning and retaining structure 20, which in this example includes an outer leg 22 and an inner leg 24. The tip also includes a sealing structure 48.

In operation, the earpiece 10 is placed in the ear and is oriented and held in place by positioning and retaining structure 20 and other portions of the earpiece. The tip 60 includes a passageway to conduct sound waves radiated by an acoustic driver in the acoustic driver module 14 to the ear canal. Extending from the tip 60 is the positioning and retaining structure 20 that holds the earpiece in position, without significant contribution from the portions of the eartip that engage the ear canal and without any structure external to the eartip. The positioning and retaining structure 20 includes at least an outer leg 22 and an inner leg 24 that are joined to other portions of the eartip at one end and are joined to each other at the other end. The outer leg is curved to generally follow the curve of the anti-helix and/or the cymba concha at the rear of the concha. In general, the compliance/stiffness of the entire positioning and retaining structure is more important than the compliance/stiffness of the material from which the positioning and retaining structure is made or the compliance/stiffness of the any one component of the positioning and retaining structure. The outer leg 22 and inner leg 24 may lie in a plane.

Figure 3:
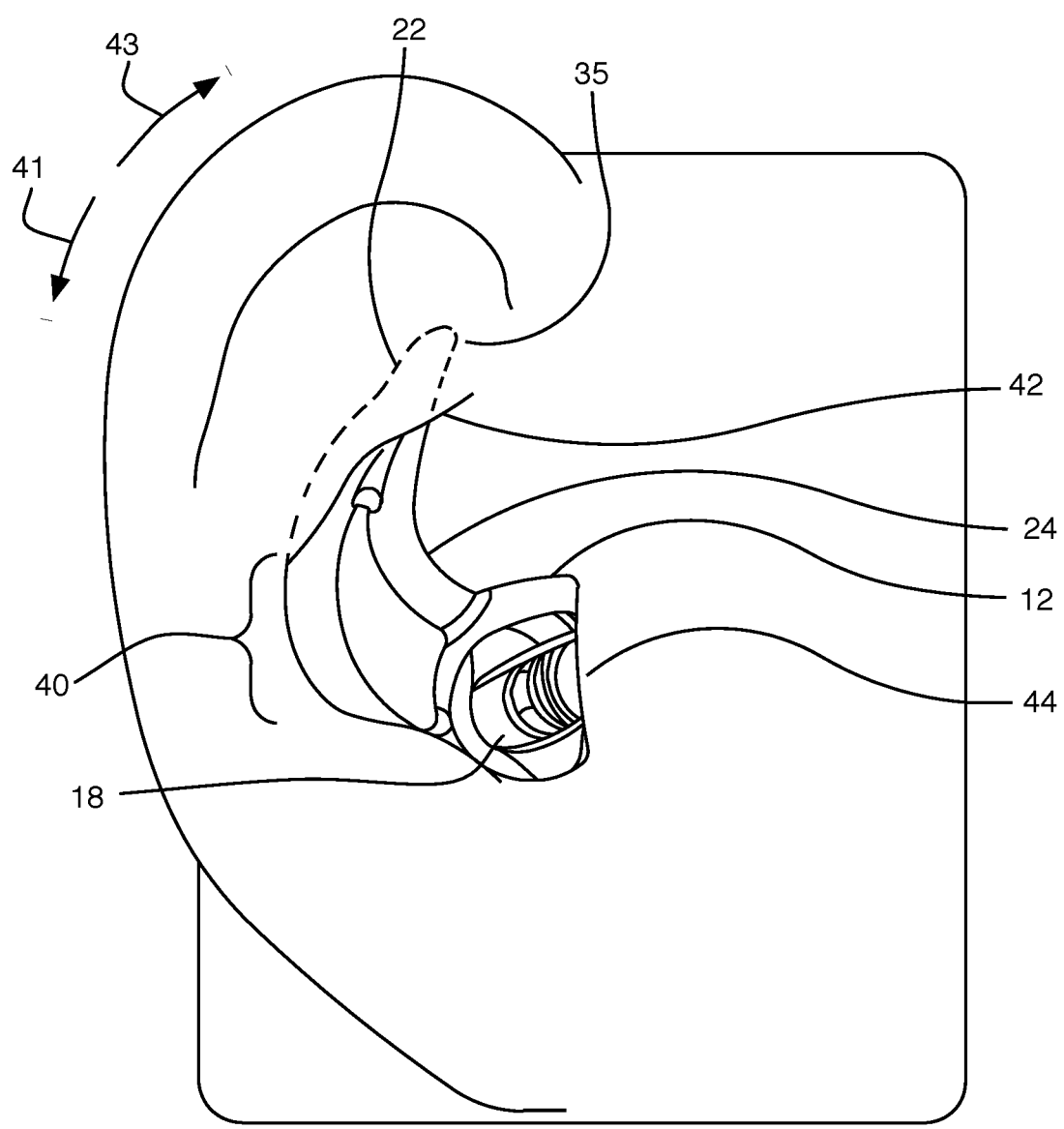
FIG. 3 is a lateral view of an earpiece and a human ear.

Referring now to FIG. 3, the earpiece tip is placed in the ear and pushed gently inward and preferably rotated counter-clockwise as indicated by arrow 43. Pushing the body into the ear causes the outer leg 22 to seat in position underneath the anti-helix, and causes the outlet section of the tip 48 (for convenience, not shown in this view) to enter the ear canal by a small amount, depending on the dimensions and geometry of the entrance to the ear canal.

The body is then rotated clockwise as indicated by arrow 41 until a condition occurs so that the body cannot be further rotated. The conditions could include: the extremity 35 of the tip may contact the base of the helix; inner leg 24 may contact the base of the helix; or the extremity 35 may become wedged behind the anti-helix in the cymba concha region. Though the positioning and retaining structure provides all three conditions (hereinafter referred to as "modes)", not all three conditions will happen for all users, but at least one of the modes will occur for most users. Which condition(s) occur(s) is dependent on the size and geometry of the user's ears.

Rotating the earpiece clockwise also causes the extremity and outer leg to engage the cymba concha region and seat beneath the anti-helix. When the body and positioning and retaining structure 20 are in place, the positioning and retaining structure and/or body contact the ear of most people in at least two, and in many people more, of several ways: a length 40 of the outer leg 22 contacts the anti-helix at the rear of the concha; the extremity 35 of the positioning and retaining structure 20 is underneath the anti-helix; portions of the outer leg 22 or tip 60 (of previous figures) or both are underneath the anti-tragus; and the tip 60 contacts at the entrance to the ear canal under the tragus. The two or more points of contact hold the earpiece in position, providing greater stability. The distributing of the force, and the compliance of the portions of the body and the outer leg that contact the ear lessens pressure on the ear, providing a more comfortable fit.

It is desirable to place the earpiece in the ear so that it is oriented properly, so that it is stable (that is, stays in the ear), so that it is comfortable, and, for some applications so that it provides significant passive attenuation of ambient noise. One way of providing stability and proper orientation is described above and is described more completely in U.S. patent application Ser. No. 12/860,531, incorporated herein by reference in its entirety.

Figure 4:
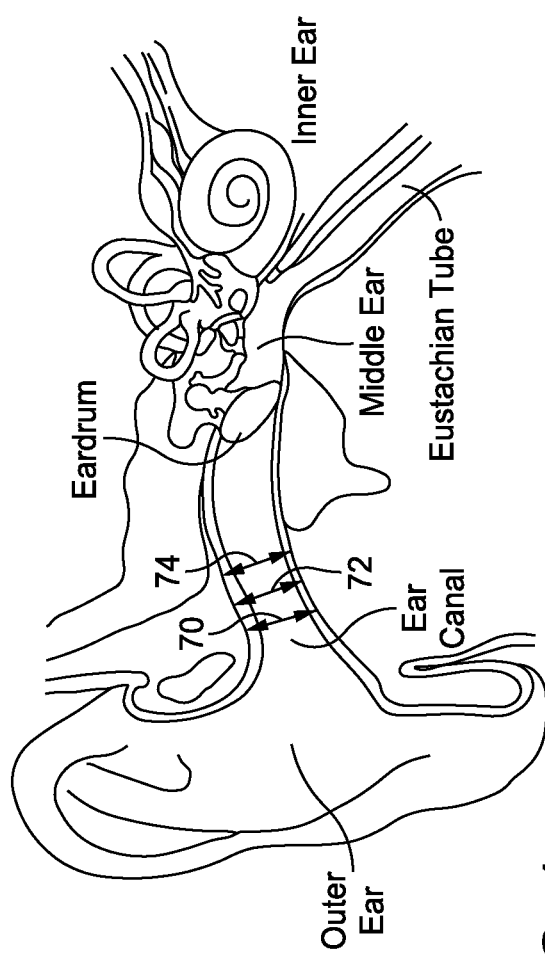
FIG. 4 shows cross-sections of two exemplary human ears.
Figure 4:
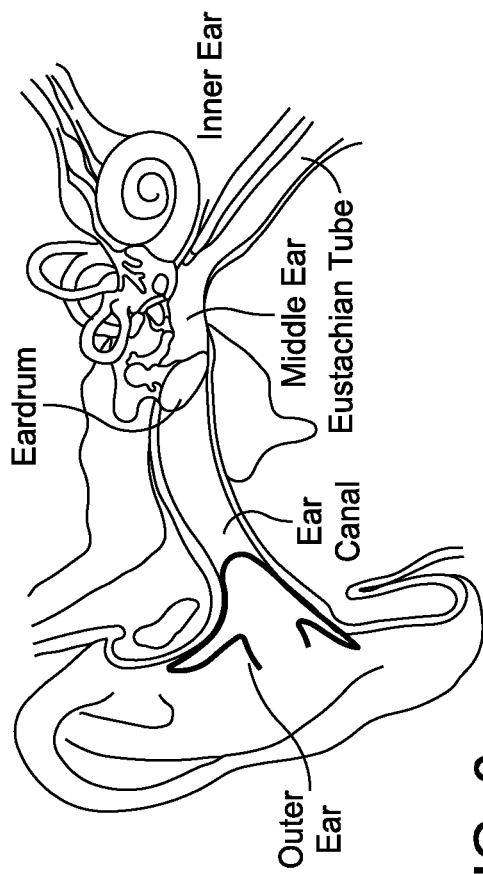

One apparatus for providing significant passive attenuation is a structure (for example a "Christmas tree" structure, as described in U.S. Pat. App. 2004/0163653, a "mushroom" structure, as described by U.S. Pat. No. 5,957,136, or disk shaped flanges, such as described in U.S. Pat. No. 6,129,175, or similar structures) that fit in the main portion of the ear canal and seals to the ear canal itself by exerting radial pressure on the walls of the main portion of the ear canal, as indicated by arrows 70, 72, and 74 of FIG. 4. The radial pressure may result from, or be supplemented by, inward clamping pressure. This apparatus may have some undesirable side effects, such as poor sealing, discomfort, or even pain, because the geometry and size of ear canals vary widely from individual to individual and because the apparatus may intrude farther into the ear canal than desired in some individuals. The main portion of the ear canal, particularly close to the middle ear, is very sensitive, so the farther the structure extends into the ear, the more uncomfortable it is likely to be. Another apparatus for providing significant passive attenuation is structure, apart from the earpiece itself, that provides inward clamping pressure that urges a conformable structure against the side of the head or the side of the ear. Examples include headbands of conventional headphones and yokes of stethoscopes, for example as described in U.S. Pat. No. 4,055,233. However, for in-the-ear earpieces, light weight and small size are desirable features, and headbands and yokes add weight and structure.

The earpiece of FIG. 2 includes a tip that provides orientation, stability, and good sealing to the entrance to the ear canal and to ear structure outside the ear canal, without excessive radial pressure, and without inward clamping pressure provided by a source not included in the earpiece.

Figure 5A:
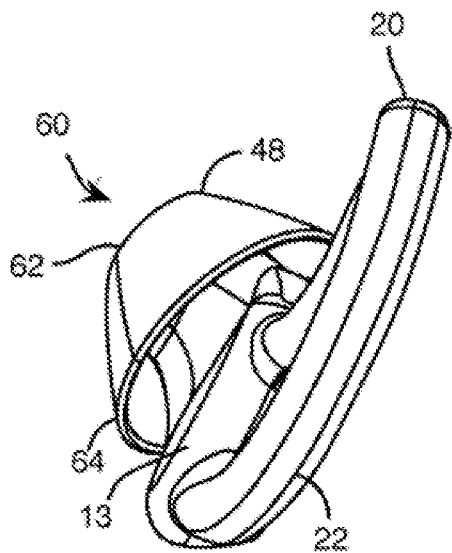
FIGS. 5A-5D are views of an earpiece.
Figure 5B:
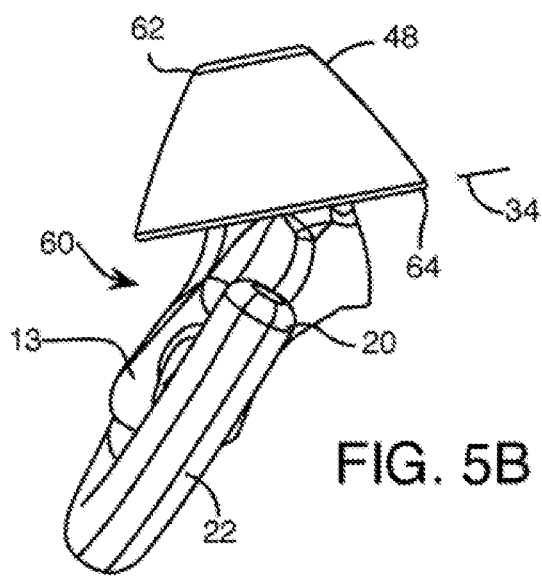
Figure 5C:
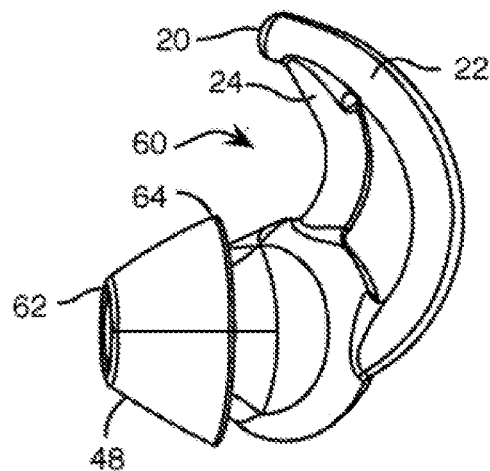
Figure 5D:
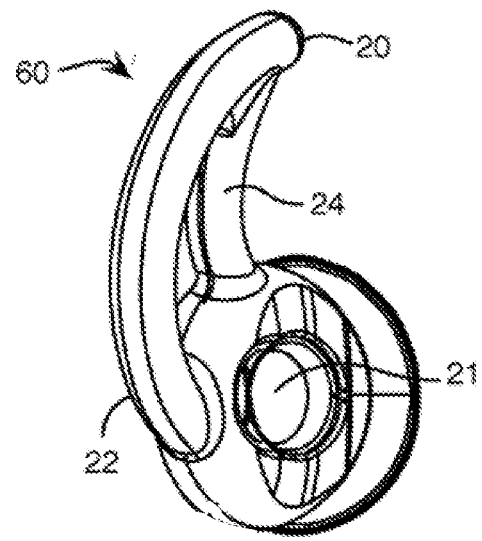

FIGS. 5A-5D shows several views of the tip 60. Not all elements of the tip 60 are identified in all of the views. The tip 60 includes positioning and retaining structure 20, a passageway 21, and sealing structure 48. The sealing structure 48 comprises a frusto-conical structure. The frusto-conical structure may have an elliptical or oval cross section (as viewed in FIG. 7A below), with walls that taper (as viewed in FIGS. 7B, 8A and 8B below) substantially linearly. In one implementation, the structure of the sealing structure and the material from which it is made cause the modulus, when measured in the direction of the arrow 34 of FIG. 5B is in the range of 0.2 to 2 gf/mm. Examples of appropriate materials include silicones, TPUs (thermoplastic polyurethanes) and TPEs (thermoplastic elastomers).

The smaller end 62 of the tip is dimensioned so that it fits inside the ear canal of most users by a small amount and so that the sealing structure 48 contacts the entrance to the ear canal but does not contact the inside of the ear canal. The larger end 64 of the tip is dimensioned so that it is larger than the entrance to the ear canal of most users.

The positioning and retaining structure 20 and the sealing structure 48 may be a single piece, made of the same material, for example a very soft silicone rubber, with a hardness of 30 Shore A or less. The walls of the sealing structure 48 may be of a uniform thickness which may be very thin, for example, less than one mm at the thickest part of the wall and may taper to the base of the frusto-conical structure so that the walls deflect easily, thereby conforming easily to the contours of the ear and providing a good seal and good passive attenuation without exerting significant radial pressure on the ear canal. Since the different parts of the earpiece serve different functions, it may be desirable for different portions of the earpiece to be made of different materials, or materials with different hardnesses or moduli. For example, hardness (durometer) of the retaining structure 20 may be selected for comfort (for example 12 Shore A), the hardness of the tip 48 may be slightly higher (for example 20 Shore A) for better fit and seal, and the hardness of the part of the eartip that mechanically couples the eartip to the acoustic module 14 may be higher (for example 70 Shore A) for better retention and seal to the part of the eartip that mechanically couples the eartip to the acoustic module 14 and in some instances so that the passage through which sound waves travel has a more consistent shape and dimensions.

Figure 6:
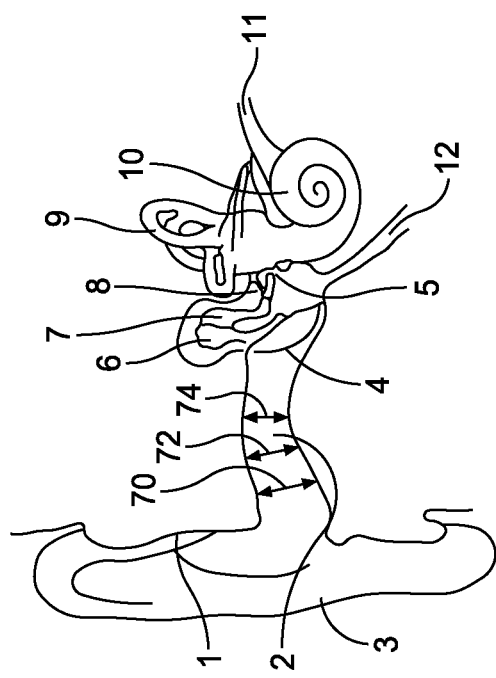
FIG. 6 shows cross-sections of two exemplary human ears.
Figure 6:
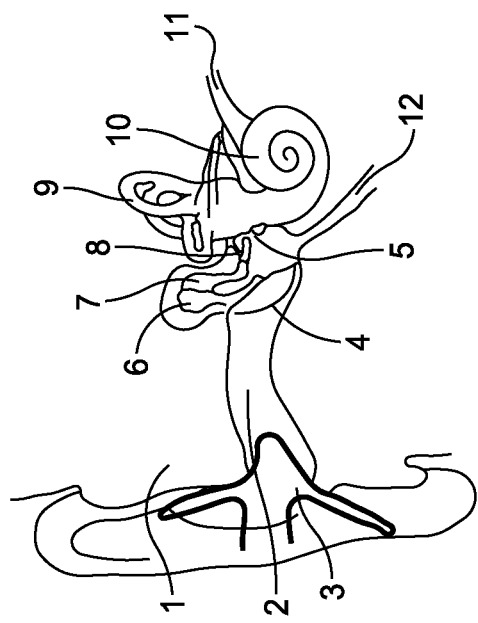

An eartip according to FIGS. 5A-5D seals to the entrance of the ear canal to provide passive attenuation and exerts little radial pressure against the main portion of the ear canal, or does not contact the main portion of the ear canal at all, as shown in FIG. 6

FIGS. 7A-7C show external views and FIGS. 8A and 8B show cross-sectional views, of the tip 60, with dimensions from a typical embodiment. In the implementations of FIGS. 7A-7C and 8A and 8B, the sealing structure 48 is elliptical, with a major axis of 7.69 mm and a minor axis of 5.83 mm at the smaller end, and a major axis of 16.1 mm and a minor axis of 14.2 mm at the larger end. A sealing structure with these dimensions fits into the ear canal of many users so that the smaller end protrudes into the ear canal by a small amount and does not contact the walls of the ear canal, so that the larger end does not fit in the ear canal, and so that the sealing structure 48 engages the entrance to the ear canal. Smaller or larger versions may be used for users with below- or above-averaged-sized ear, including children. Versions with similar overall size but different aspect ratios between major and minor axes may be provided for users with ear canal entrances that are more- or less-circular than average.

Numerous uses of and departures from the specific apparatus and techniques disclosed herein may be made without departing from the inventive concepts. Consequently, the invention is to be construed as embracing each and every novel feature and novel combination of features disclosed herein and limited only by the spirit and scope of the appended claims.

What is claimed is:

1. An ear tip for an in-ear earpiece, comprising:
    a body configured to fit within the concha of a wearer's ear;
    an outlet extending towards the ear canal of the wearer's ear when the ear tip is placed in the wearer's ear, the outlet comprising an acoustic passage to conduct sound waves to the wearer's ear canal;
    a sealing structure having (i) a base with an outer surface extending from a first end contacting an end of the outlet to a second end that contacts the flesh of the entrance of the ear canal of the wearer's ear and (ii) a conical wall extending from the second end towards the first end at a non-right angle relative to the outer surface of the base, wherein the sealing structure has a substantially uniform thickness; and
    a retaining structure extending from the body and shaped to generally follow the curve of the antihelix of the wearer's ear, wherein, when the ear tip is placed in an ear,
        the retaining structure applies anchoring pressure to the antihelix of the wearer's ear to orient the body and the sealing structure so that the sealing structure is positioned at the entrance of the ear canal,
        the sealing structure forms a substantial seal with the flesh of the entrance of the ear canal of the wearer's ear, and
        the sealing structure is positioned such that any pressure applied to the flesh of the entrance of the wearer's ear canal by the sealing structure does not contribute to holding the ear tip in the wearer's ear.

2. The ear tip of claim 1, wherein the sealing structure seals the entrance to the ear canal by conforming to the entrance to the ear canal when pressed towards the ear canal.

3. The ear tip of claim 1, wherein the sealing structure comprises a frusto-conical sealing structure and wherein the sealing structure is joined to the outlet at a narrow end of the frusto-conical sealing structure.

4. The ear tip of claim 3, wherein a wide end of the frusto-conical sealing structure is larger than a width of a typical ear canal.

5. The ear tip of claim 1, wherein the body has a generally planar surface that rests against at least a portion of the wearer's concha.

6. The ear tip of claim 5, wherein the outlet extends from the body at a non-right angle relative to the generally planar surface of the body.

7. The ear tip of claim 1, wherein the sealing structure comprises a thin layer of material that at least partially surrounds the outlet.

8. The ear tip of claim 7, wherein the thin layer of material has a hardness of approximately 30 Shore A or less.

9. The ear tip of claim 1, wherein the acoustic passage is substantially elliptical in cross-section.

10. The ear tip of claim 1, wherein the retaining structure comprises a material having a different hardness than a material of the sealing structure.

11. The ear tip of claim 10, wherein the outlet comprises a material having a different hardness than the material of the retaining structure and a different hardness than the material of the sealing structure.

12. An ear tip for an in-ear earpiece, comprising:
    a body configured to fit within and rest against at least a portion of the concha of a wearer's ear;

an outlet extending at a non-right angle relative to a generally planar surface of the body and towards the ear canal of the wearer's ear when the ear tip is placed in the wearer's ear, the outlet comprising an acoustic passage to conduct sound waves to the wearer's ear canal;

a sealing structure having (i) a base with an outer surface extending from a first end contacting an end of the outlet to a second end that contacts the flesh of the entrance of the ear canal of the wearer's ear and (ii) a conical wall extending from the second end towards the first end at a non-right angle relative to the outer surface of the base, wherein the sealing structure extends from the end of the outlet such that a central axis of the sealing structure is at substantially the same non-right angle relative to the generally planar surface of the body as of the outlet, and wherein the sealing structure has a substantially uniform thickness; and a retaining structure extending from the body and shaped to generally follow the curve of the antihelix of the wearer's ear;

wherein, when the ear tip is placed in an ear,
the retaining structure is seated underneath at least a portion of the antihelix of a wearer's ear and applies anchoring pressure to the antihelix of the wearer's ear to orient the body and the sealing structure so that the sealing structure is positioned at the entrance of the ear canal,
the sealing structure forms a substantial seal with the flesh of the ear canal of the wearer's ear, and
the sealing structure is positioned such that any pressure applied to the flesh of the entrance of the wearer's ear canal by the sealing structure does not contribute to holding the ear tip in the wearer's ear.

13. The ear tip of claim 12, wherein the sealing structure comprises a frusto-conical shape, and the sealing structure is joined to the outlet at a narrow end of the frusto-conical shape, and a wide end of the frusto-conical shape is larger than a typical ear canal is wide.

14. The ear tip of claim 12, wherein the sealing structure comprises a thin layer of material that has a hardness of approximately 30 Shore A or less.

15. The ear tip of claim 12, wherein the body is coupled to an acoustic driver of the earpiece, the acoustic passage of the outlet comprising an opening in the body for receiving sound waves from the acoustic driver of the earpiece.

16. The ear tip of claim 12, wherein the acoustic passage is substantially elliptical in cross-section.

17. The ear tip of claim 12, wherein the retaining structure comprises a material having a different hardness than a material of the sealing structure, and the outlet comprises a material having a different hardness than the material of the retaining structure and a different hardness than the material of the sealing structure.

18. An ear tip for an in-ear earpiece, comprising:
a disc-shaped base;
an outlet extending from the base at a non-right angle relative to a plane of a surface of the base;
a frusto-conical flap having (i) a base with an outer surface extending from a first end contacting an end of the outlet to a second end that contacts the flesh of the entrance of the canal of the wearer's ear and (ii) a conical wall extending from the second end towards the first end at a non-right angle relative to the outer surface of the base, wherein the flap surrounds the outlet such that a central axis of the flap is at substantially the same non-right angle relative to the plane of the surface of the base as the outlet, with a narrow end of the flap joined to the end of the outlet, and the flap having a substantially uniform thickness; and
a retaining leg extending from and curving around at least a portion of the base,
wherein, when the ear tip is placed in a wearer's ear,
the retaining leg is seated underneath the antihelix of the wearer's ear and applies anchoring pressure to the antihelix of the wearer's ear to orient the base and the flap so that the flap is positioned at the entrance of the ear canal,
the flap forms a substantial seal with the flesh of the entrance of the wearer's ear canal, and
the flap is positioned such that any pressure applied to the flesh of the entrance of the wearer's ear canal by the flap does not contribute to holding the ear tip in the wearer's ear.

19. The ear tip of claim 18, wherein the flap has a stiffness to maintain a gap between the flap and the outlet absent external forces.

20. The ear tip of claim 18, wherein the base prevents the outlet and flap from contacting the ear canal beyond the ear canal entrance.

21. The ear tip of claim 18, wherein the retaining leg curves within the plane in which the disc lies.

* * * * *